United States Patent [19]

Caddy et al.

[11] Patent Number: 5,625,055
[45] Date of Patent: Apr. 29, 1997

[54] RAPID ISOLATION OF POLYNUCLEOTIDES

[75] Inventors: Brian Caddy; Jing Cheng, both of Glasgow, United Kingdom

[73] Assignee: University of Strathclyde, Glasgow, United Kingdom

[21] Appl. No.: 450,264

[22] Filed: May 25, 1995

Related U.S. Application Data

[63] Continuation of Ser. No. 30,422, filed as PCT/GB91/01612 Sep. 20, 1991, published as WO92/05181 Apr. 2, 1992, abandoned.

[30] Foreign Application Priority Data

Sep. 22, 1990 [GB] United Kingdom ............ 9020683

[51] Int. Cl.$^6$ .................................. C07H 21/04
[52] U.S. Cl. ................ 536/25.42; 536/25.4; 536/25.41
[58] Field of Search ................ 536/25.4, 25.41, 536/25.42

[56] References Cited

U.S. PATENT DOCUMENTS

| | | | |
|---|---|---|---|
| 4,090,022 | 5/1978 | Tsao et al. | 536/57 |
| 4,352,884 | 10/1982 | Nakashima et al. | 435/180 |
| 4,554,088 | 11/1985 | Whitehead et al. | 252/62.54 |
| 4,695,392 | 9/1987 | Whitehead et al. | 252/62.54 |
| 4,695,393 | 9/1987 | Whitehead et al. | 252/62.54 |
| 4,822,681 | 4/1989 | Schlosser et al. | 428/405 |
| 4,923,978 | 5/1990 | McCormick | 536/25.4 |
| 5,055,426 | 10/1991 | James et al. | 501/80 |
| 5,106,966 | 4/1992 | Thomas et al. | 536/25.4 |
| 5,175,271 | 12/1992 | Thomas et al. | 536/26.13 |

FOREIGN PATENT DOCUMENTS

| | | |
|---|---|---|
| 0088818 | 9/1983 | European Pat. Off. . |
| 9102740 | 3/1991 | WIPO . |
| 9215674 | 9/1992 | WIPO . |

OTHER PUBLICATIONS

Vandenberg et al., "Protein Immobilization to 3–Aminopropyl Triethoxysilance/Glutaraldehyde Surfaces: Characterization by Detergent Washing," *J. Colloid Interface Sci.*, 143(2), 327–335 (1991); *Chem. Abstr.*, 114(23), p. 457, Abstr. No. 225132s (1991); only Abstract provided.

Kopeckova et al., "The Influence of Poly(ethylene oxide) Spacers of the Covalent and Non–specific Binding of Immunoglobulin G to Silica Surfaces," *New Polym. Mater.*, 1(4), 289–297 (1990); *Chem. Abstr.*,115(9), p. 404, Abstr. No. 88658x (1991); only Abstract provided.

*Aldrich Catalog/Handbook of Fine Chemicals*, Aldrich Chemical Company, Milwaukee, WI, 1990, p. 1150, items circled in red.

*Primary Examiner*—John Kight
*Assistant Examiner*—L. Eric Crane
*Attorney, Agent, or Firm*—Bell, Seltzer, Park & Gibson

[57] ABSTRACT

Polynucleotides (particularly DNA) formed from a lysate of cellular material in a holding tube are separated from proteins in a two-phase solvent system formed by a mild oxidising perchlorate and an organic solvent such as chloroform. A powder of polymerised silica gel particles containing free aldehyde (CHO) or ketone (CO) groups which react with the proteins is added to the uppermost layer which is the layer containing the polynucleotides of interest and is allowed to descend through that layer thereby cleansing it of protein contaminants. The protein reacted silica gel particles lodge at the interface between the upper polynucleotide containing layer and the lower organic solvent layer which contains the bulk of the proteins and forms a solid disc adherent to the walls of the holding tube. The uppermost layer can thereafter be decanted for precipitation of the polynucleotides therein without contamination from the protein containing solvent layer. The powder of polymerised silica gel particles is preferably prepared by cross-linking silica gel particles of particle size 250–400 mesh with 3-aminopropyltriethosilane followed by reaction with gluteraldehyde.

5 Claims, No Drawings

RAPID ISOLATION OF POLYNUCLEOTIDES

This is a continuation of application Ser. No. 08/030,422, filed as PCT/GB91/01612 Sep. 20, 1991, published as WO92/05181 Apr. 2, 1992, now abandoned.

The present invention relates to a process for the isolation of polynucleotides (particularly oligonucleotides and DNA) from mixtures with proteins and materials for use in the process. In particular, the invention is concerned with the isolation of DNA from mixtures of DNA and cellular proteins produced by the lysis of lymphocytes (white blood cells).

The requirement to provide samples of substantially pure DNA free from cellular proteins may arise in a number of instances where there is a need to investigate the detailed DNA structure of an individual.

In the field of forensic science, the technique of genetic fingerprinting involves the identification of individual persons on the basis of their unique DNA structure. Within a person's DNA are a number of "hypervariable regions" which are unique to the individual, yet include common core sequences. No two individuals share the same set of hypervariable regions (except identical twins). The fingerprint is produced by controlled digestion of the DNA using a set of restriction enzymes, slab gel electrophoresis and Southern blotting, followed by extraction of restriction fragment length polymorphisms using hybridisation probes specific to the core sequences.

In order to carry out genetic fingerprinting, a sample of substantially pure DNA is required and this is usually obtained from a sample of whole blood. The blood sample is processed by separation of the lymphocytes therefrom, lysis of the lymphocytes to yield mixtures of DNA and proteins, and separation of the DNA from the mixture. Since the available blood sample (for example, from the scene of a crime) may be only small, it is important that the DNA isolation procedure be as efficient as possible.

Techniques are becoming available for the diagnosis of genetically related diseases which depend on investigating the DNA structure for genetic defects. Tests may be carried out on putative parents where one or both parent has a family history including the disease, in order to establish the likelihood of the baby having the disease.

Cellular material may also be obtained from fetal blood samples or samples of amniotic fluid for direct diagnosis of genetic disorders prior to birth. In the future there is the hope that gene therapies may become available for remedying the missing or mutant gene.

In conventional DNA isolation processes, the lymphocytes are lysed using a lysis buffer containing sodium dodecyl sulphate (SDS) to solubilize the cell membranes. The lysis mixture contains DNA and cellular proteins, possibly in intimate association. The mixture is incubated overnight at 37° C. with proteinase K which digests the proteins. The SDS buffer also acts to activate proteinase K. The proteins are digested into smaller peptide fragments by fission at the peptide bonds. The protein fragments are then denatured and removed from the mixture employing sequential extractions using phenol, phenol/chloroform mixture and chloroform. The function of the phenol is to denature the proteins. Use of phenol/chloroform mixtures inhibits RNase enzyme activity. The final extraction with chloroform (using chloroform/isoamyl alcohol 24:1 v/v) removes any residual traces of phenol from the DNA preparation. Finally, the DNA is concentrated using absolute alcohol.

There are a number of problems associated with the conventional method. Firstly, the overnight incubation with proteinase K causes partial degradation of high molecular weight DNA. This is due to the lengthy incubation period during which the DNA is exposed to degradation resulting from any residual cellular nucleases present in the lysis mixture or from the proteinase K preparation used. Also phenol is toxic and its use poses a safety hazard to operators, and there are associated problems of safe disposal.

Furthermore, the yield of DNA is relatively low and can only be improved by time-consuming repeated extractions.

Extraction with chloroform results in a lower protein-containing chloroform layer and an upper aqueous layer containing DNA. However, the separation into layers is incomplete and an intermediate aqueous layer containing DNA and protein tends to be present, which makes the efficient separation of the aqueous layer from the organic layer very difficult. This can only be achieved by repeated solvent extractions. Moreover, the DNA which is always present in the upper layer, is usually withdrawn by suction and the shear forces associated with this technique tend to cause degradation of the DNA especially when repeated extractions are required. Even with the repeated time consuming extractions, the maximum purity obtainable is reflected in an absorbance ratio of about 1.7. This is the ratio of absorbance at 260 nm (DNA) to that at 280 nm (protein).

It is an object of the present invention to mitigate these problems by providing an improved process for the isolation of DNA by removal of proteins from DNA/protein mixtures.

In essence, the present invention involves the absorption of proteins to form a solid or semi-solid material, particularly using a material having free CHO or CO groups which react with primary amine groups present on the proteins.

The present invention provides a process for the isolation of polynucleotides from aqueous mixtures containing the polynucleotides and proteins, which comprises;

adding an organic solvent to the aqueous mixture to form a two-phase solvent extraction system;

adding a material which is reactive with the proteins (and non-reactive to polynucleotides) and which absorbs the proteins to form a solid or semi-solid material containing the proteins, the solid or semi-solid protein-containing material having a density such as to form a layer intermediate said organic layer and said aqueous layer; and separating the aqueous layer containing the polynucleotides from said protein-containing material.

Specifically, one aspect of the present invention provides a process for the isolation of DNA from cells, which comprises:

(a) lysing the cells to form a lysate containing DNA and free proteins, (b) exposing the lysate to a material which is reactive with proteins (and non-reactive to DNA) and which absorbs the proteins to form a solid or semi-solid material containing said proteins; and (c) separating the DNA from said protein-containing material.

The protein absorbing material preferably contains free CHO (aldehyde) or CO (ketone) groups reactive with proteinaceous primary amino groups, and is usually a polymerised material.

The protein absorbing material may be prepared by cross-linking a hydroxyl-containing substrate material. Such substrate materials are well known in the field of chromatography and it is preferred in the present invention to employ a silica. Other possible hydroxyl-containing polymers include polyethylene or polypropylene glycols, polystyrenes having OH substituents in the ring or on aliphatic side chains, and polyacrylate glycol monoesters.

Cross-linking may be carried out using a cross-linking agent which either contains CHO or CO groups, or which can be reacted further so as to introduce free CHO or CO groups. Preferably, the cross-linking agent comprises polyalkoxy groups which react with the free hydroxyl groups on the substrate, eliminating alcohol. The present invention preferably employs an alkoxysilane of general formula (I)

$$(R^1O)_3 Si-R^2-NH_2 \quad (I)$$

Where $R^1$ is $C_1-C_6$ alkyl, and
$R^2$ is $C_1-C_6$ alkylidene.

The preferred cross-linking agent is 3-aminopropyltriethoxysilane. This compound contains an amino substituent which may be further reacted to introduce free CHO or CO groups, for example, by reaction with a dialdehyde or haloaldehyde of general formula (II).

$$X-(CH_2)_n-CR^3O \quad (II)$$

where X is $CR^3O$ or halo (preferably chloro),
$R^3$ is H or $C_1-C_6$ alkyl, and
n is 3 to 10 (preferably 3 to 5).

The preferred reagent is glutaraldehyde OHC $(CH_2)_3$ CHO. The value of n may be varied to vary the chain length in order to improve access of the proteins to the CHO or CO groups respectively.

The resulting cross-linked protein absorbing material is usually solid or semi-solid to facilitate use in separation from the DNA-containing solution. However, reaction of the free CHO or CO groups with digested or undigested protein also results in some cross-linking, so that the invention also envisages the use of materials which, irrespective of their original form, are converted by reaction with proteins into solid or semi-solid materials which can be readily separated from the DNA-containing solution.

It is particularly preferred, that the protein cross-linking step produces a solid mass of cross-linked material, thereby further facilitating separation.

In a preferred embodiment, isolation of DNA is achieved in a two-phase solvent extraction system, wherein the aqueous DNA solution is present as the upper layer. In this case the density of the material containing absorbed protein is preferably arranged such that it forms an intermediate layer between the upper aqueous layer and the lower solvent layer, so as to assist complete removal of the aqueous DNA-containing layer without contamination from the solvent layer.

Where a silica-based protein absorbing material is used, it is preferred to use silica gel of a particle size 250–400 mesh in order to provide a solid cross-linked mass when reacted with protein.

The DNA is generally derived from lymphocytes, though the invention may also be applied to DNA obtained from other cell types. The technique of the present invention is also applicable to the separation of oligonucleotides in general from proteins. For example, the technique may be used to separate DNA restriction fragments from mixtures with restriction enzymes (which are proteins). Such mixtures are produced for example in the digestion of DNA by restriction enzymes in order to produce restriction fragments for gel electrophoresis separation in DNA fingerprinting procedures.

The lysis of the cells is preferably carried out using a surfactant, such as SDS buffer.

Since at least some of the DNA and protein present in the lysis mixture may be intimately associated, it is preferred to denature the proteins (e.g. by heating). Although not essential, it is also preferred to digest the proteins to reduce their chain length prior to treatment with the protein absorbing material. This may be carried out using proteinase K and chloroform as in the conventional method; but this suffers from the disadvantage described earlier in this specification. In a preferred embodiment of the invention, a mild oxidising agent such as sodium perchlorate (optionally together with a surfactant and heating but freshly prepared and filtered (0.25–0.45 microns)) is used to denature and digest the proteins. Contrary to previous belief, it has been surprisingly found that mild oxidising agents may be employed without degrading the DNA itself.

The preferred embodiment allows the isolation of DNA to be carried out much more speedily than using the conventional method. Moreover, the DNA is obtained in high yield and with improved purity.

Embodiments of the present invention will now be described by way of example only.

EXAMPLE 1

PREPARATION OF PROTEIN-ABSORBING MATERIAL (Polymerisation of Silica Gel)

50 grams of dried particulate silica gel (250–400 mesh) was activated by addition of 300 mL of 5% nitric acid. One hour later the silica gel was washed with 1000 mL of double distilled water and then 400 mL of HPLC grade methanol using a vacuum pump.

The pH value of 300 mL of 10% 3-aminopropyltriethoxysilane $(C_2H_5O)_3-S-CH_2CH_2CH_2 NH_2$ (APTES) was adjusted to 3.5 with 6N hydrochloric acid. The solution was then added to the above silica gel. The reactants were put in a 75° C. water bath for 2 hours and then washed with 500 mL of double distilled water. The treated silica gel was then dried in a 115° C. oven for at least 5 hours.

The pH value of 400 mL aqueous glutaraldehyde OHC— $(CH_2)_3$—CHO (2.5%) was adjusted to 7.0 and the solution was then added to the treated silica gel. The reaction was allowed to proceed at room temperature for 2 hours with stirring. The resulting polymerised silica gel was then thoroughly washed with 1000 mL of deionised double distilled water, and then drained using a vacuum pump, to yield a free-flowing powder.

EXAMPLE 2

ISOLATION OF DNA FROM LYMPHOCYTES

The removal of proteins (mainly histone proteins associated with DNA) present in the lysis solution is a key step in the purification of genomic DNA and was carried out as follows.

(a) Preparation of Lymphocytes

To a 2.0 mL volume autoclaved Eppendorf tube was added 550 uL EDTA treated whole blood (500 uL whole blood+50 uL of 2% aqueous EDTA) and 1.45 mL of buffer A (lymphocytes extraction buffer). The mixture was left at room temperature for 6.0 min with occasional gentle inversion of the containing vessel and then centrifuged at 2040×g for 4.0 min. The supernatant was removed immediately to leave a lymphocyte cell pellet. Experiment shows that it is best to use small diameter tubes, e.g. 2 mL tube 7–8 mm diameter.

| Buffer A: | 10 mM | Tris-HCl |
| --- | --- | --- |
| | 320 mM | Sucrose |
| | 5 mM | MgCl$_2$ |
| | 1% | Triton X-100, pH 7.5 |

(b) Lysis of Lymphocytes

The isolated lymphocyte cell pellet was resuspended in 500 uL of buffer B (lysis buffer) and 125 uL of 5M sodium perchlorate solution was added at once. After being well mixed gently, the content was heated at 37° C. for 20 mins and then at 60° C. for a further 20 mins before being cooled. This treatment caused lysis of the lymphocytes, denaturing and partial digestion of the protein to provide a lysis mixture.

| Buffer B: | 400 mM | Tris-HCl pH 8.0 |
| --- | --- | --- |
| | 60 mM | EDTA |
| | 150 mM | NaCl |
| | 1% | SDS |

(c) Isolation and Concentration of DNA

An equal volume of chloroform was added to the lysis mixture obtained above and subjected to very gentle inversion of the containing vessel for 5 mins and then spun at 82×g for 2 mins (horizontal centrifuge). After adding 120 mg of protein absorbing material in the form of polymerised silica gel powder produced in Example 1 without any mixing, the mixture was centrifuged at once at 735×g for 2 mins. If possible it is preferred to use horizontal centrifugation. The amount of polymerised silica gel which is used is partly dependent upon the diameter of the analytical tubes used for extraction. The amount cited refers to tubes of 2 mL volume having a diameter of 7–8 mm. It is sufficient if a 1–2 mm layer thickness is formed after centrifugation for success of the technique. After the tube was removed from the centrifuge it was seen that the silica gel was positioned between the top aqueous layer (containing the desired DNA) and the bottom organic layer as a hard disk adhered to the tube wall with proteins trapped inside. The aqueous layer was transferred to another 2 mL volume tube and two volumes of 4° C. absolute alcohol was immediately added. After the mixture was gently mixed for 15 secs. by inverting the tube, a fibrous network form of DNA was precipitated out and the supernatant was removed. Then 95% alcohol was used to wash the DNA pellet. The supernatant alcohol was removed and the purified DNA was dried in a vacuum dessicator for 10 min. The purified and dried DNA was finally redissolved in 50 uL of TE buffer and was ready for DNA fingerprinting.

| TE Buffer: | 10 mM | Tris-HCl |
| --- | --- | --- |
| | 1 mM | EDTA pH 7.5(d) RESULTS |

The whole process took less than two hours instead of 8 to 15 hours using the conventional method. The yield of DNA was about 10 ug per 500 ul of whole blood which demonstrates approximately a 100% improvement over the more usual 4.0 to 6.0 ug per 500 ul of whole blood obtained from the conventional extraction procedure. Moreover, the high purity of the DNA produced by this new one step method is attested to by the consistantly obtained value of 1.8 or higher for the UV absorbance ratio of DNA at 260 mm to protein at 280 mm compared with normal values of 1.3 to 1.4 obtained by the conventional method. Since these values are expressed on a logarithmic scale, the purities obtained according to the present invention are in fact approximately twice as high as those normally obtainable using conventional techniques. Values of 1.7 are the best which can be obtained by the conventional method but this requires several deleterious transfers. In addition the new method permits the processing of 45 ul samples of whole blood in contrast to the 60 ul of the conventional method.

By the running of mini-gel electrophoresis it can be seen that the extracted DNA shows fewer degradations than when the conventional method is used.

We claim:

1. A process for the isolation of polynucleotides from isolated cellular material, the process comprising the sequential steps of:
    i) suspending the cellular material in a lysis buffer within a holding tube so as to render the protein content of the cellular material accessible to a denaturing agent;
    ii) denaturing and digesting the protein content in the holding tube by adding to the holding tube a mild oxidising agent which is free of both phenol and proteinase K and incubating the mixture thereafter, whereby to form an aqueous mixture of the polynucleotides and proteins in the holding tube;
    iii) forming a two phase solvent extraction system by adding to the tube and mixing with the aqueous mixture therein an immiscible organic solvent which extracts the proteins and results in a lower protein-containing solvent layer, an upper aqueous layer containing polynucleotides and an intermediate aqueous layer containing polynucleotides and proteins; and
    iv) scavenging proteins from the aqueous layers by adding to the two phase system in the tube, without mixing of the layers, a powder of polymerised silica gel particles containing free aldehyde (CHO) or ketone (CO) groups which react with the proteins,
    the arrangement being such that the particles descend through the aqueous layers, reactively binding proteins from the aqueous layers, and form a solid disc adherent to the walls of the tube at the interface between the aqueous and organic solvent layers so that thereafter the aqueous polynucleotide containing layer can be completely removed from the tube for precipitation of the polynucleotides therein without contamination from the protein-containing solvent layer.

2. A process for the isolation of polynucleotides from isolated cellular material, the process comprising the sequential steps of:
    i) suspending the cellular material in a lysis buffer within a holding tube so as to render the protein content of the cellular material accessible to a denaturing agent;
    ii) denaturing and digesting the protein content in the holding tube by adding to the holding tube a mild oxidising perchlorate which is free of both phenol and proteinase K and incubating the mixture thereafter, whereby to form an aqueous mixture of the polynucleotides and proteins in the holding tube;
    iii) forming a two phase solvent extraction system by adding to the tube and mixing with the aqueous mixture therein an immiscible organic solvent which extracts the proteins and results in a lower protein-containing solvent layer, an upper aqueous layer containing polynucleotides and an intermediate aqueous layer containing polynucleotides and proteins; and
    iv) scavenging proteins from the aqueous layers by adding to the two phase system in the tube, without mixing of the layers, a powder of polymerised silica gel particles containing free aldehyde (CHO) or ketone (CO) groups which react with the proteins, the particles having a mesh size in the range 250–400, the arrangement being such that the particles descend through the aqueous layers, reactively binding proteins from the aqueous layers, and form a solid disc adherent to the walls of the tube at the interface between the aqueous and organic solvent layers so that thereafter the aqueous polynucleotide containing layer can be completely removed from the tube for precipitation of the polynucleotides therein without contamination from the protein-containing solvent layer.

3. The process of claim 1 or claim 2 wherein the material which is reactive to proteins has been prepared by
(i) cross-linking silica gel particles with an alkoxysilane of general formula (I)

$$(R^1O)_3\text{Si}-R^2-NH_2 \quad \text{(I)}$$

where $R^1$ is $C_{1-6}$ alkyl, and $R^2$ is $C_{1-6}$ alkylidene;
and (ii) reacting the cross-linked particles with an amino-reactive compound of general formula (II)

$$X-(CH_2)_n-CR^3O \quad \text{(II)}$$

where X is $CR^3O$ or halo; $R^3$ is H or $C_{1-6}$ alkyl; and n is 3 to 10.

4. The process of claim 3, wherein the cross-linking agent of general formula (I) is 3-aminopropyltriethoxysilane; and the amino-reactive compound of general formula (II) is gluteraldehyde.

5. The process of claim 1 wherein the mind oxidising agent is a perchlorate.

* * * * *